United States Patent [19]

Tamion

[11] Patent Number: 5,998,608
[45] Date of Patent: Dec. 7, 1999

[54] METHOD OF MANUFACTURING AN ALDOSE OR AN ALDOSE DERIVATIVE

[75] Inventor: M. Rodolphe Tamion, Allouagne, France

[73] Assignee: Roquette Freres, Lestrem, France

[21] Appl. No.: 09/166,956

[22] Filed: Oct. 6, 1998

[30] Foreign Application Priority Data

Oct. 7, 1997 [FR] France ................................ 97 12477

[51] Int. Cl.$^6$ .............................. C07K 1/00; C07K 3/02
[52] U.S. Cl. ........................................ 536/124; 536/1.11
[58] Field of Search ................................ 536/1.11, 124

[56] References Cited

U.S. PATENT DOCUMENTS

| | | | |
|---|---|---|---|
| 3,755,294 | 8/1973 | Walon | 536/124 |
| 4,845,208 | 7/1989 | Fuertes et al. | 562/515 |

FOREIGN PATENT DOCUMENTS

| | | |
|---|---|---|
| 232647 | 12/1986 | Czech Rep. . |
| 279002 | 9/1990 | Czech Rep. . |
| 0 233 816 | 8/1987 | European Pat. Off. . |
| 0 716 067 | 6/1996 | European Pat. Off. . |
| 0 810 292 | 12/1997 | European Pat. Off. . |
| 0 829 485 | 3/1998 | European Pat. Off. . |

OTHER PUBLICATIONS

Berichte (1899), vol. 32 pp. 3672–3681 (Ruff).
Berichte (1900), vol. 33 pp. 1798–1811 (Ruff et al).
Journal of the American Chemical Society (1934), vol. 56, p. 1632–1633 (Hockett & Hudson) (Jul. 1934).
Journal of the American Chemical Society (1950), vol. 72, p. 4546 (Fletcher et al.

Yanagihara et al., "Preparation of 2–Hydroxymethylated Aldose by the Stereospecific Rearrangement of Ketose," *Bull. Society Chemistry Japan*, 68(1), 237–242 (Jan., 1995).

Yano et al., "Reactions of Metal Complexes with Carbohydrates: Synthesis and Characterization of Novel Nickel(II) Complexes Containing Glycoslamines Derived From a Monossaccharide and a Diamine. An X–Ray Crystallographic Study of (Ethylenediamine){N–(2–aminoethyl)–D–fructopyranosylamine}nickel(II) • $Cl_2$ • $CH_3OH$," *Carbohydrate Research*, 142(2), 179–193 (Oct. 15, 1985).

Yamauchi et al., "Epimerization and Isomerization of Various Monosaccharides Using Metal–Diamine Sysems," *Carbohdrate Research*, 204, 233–239 (Sep. 5, 1990).

*Concise Encyclopedia Chemistry*, Eagleston (ed.), Walter de Gruyter, New York, NY, 1994, pp. 31, 35 and 1140.

*Primary Examiner*—L. Eric Crane
*Attorney, Agent, or Firm*—Henderson & Sturm

[57] ABSTRACT

The invention relates to a method of manufacturing an aldose or an aldose derivative, with n carbon atoms, characterised by the fact than an aqueous solution of a salt of acid derivative of monosaccharide with n+2 carbon atoms containing at least one α-hydroxy acid unit, with the exception of gluconic acid, is brought into contact with hydrogen peroxide in the presence of at least one salt of a metal chosen from the group consisting of cobalt, nickel and ruthenium.

17 Claims, No Drawings

METHOD OF MANUFACTURING AN ALDOSE OR AN ALDOSE DERIVATIVE

The subject matter of the present invention is a method of manufacturing an aldose or an aldose derivative. More precisely, the subject matter of the present invention is a method of manufacturing an aldose or an aldose derivative, with n carbon atoms, from a salt of an acid derivative of monosaccharide with n+2 carbon atoms containing at least one α-hydroxy acid unit of hydrogen peroxide, catalysed by a salt of a metal chosen from the group consisting of cobalt, nickel and ruthenium, and taking place in an aqueous phase.

In the present invention what is meant by
- "aldose" is a monosaccharide containing one aldehyde function;
- "aldose derivative" is more particularly a dialdose (monosaccharide containing two aldehyde functions) or a uronic acid (monocarboxylic acid derived from an aldose by replacing the $CH_2OH$ group with a COOH group;
- "acid derivative of monosaccharide containing at least one α-hydroxy acid unit" is a mono- or dicarboxylic acid derived from an aldose and containing one CHOH function in α of the acid function or functions.

In particular, the method of the present invention makes it possible to obtain, with an excellent yield, an aldose from an aldonic acid, a dialdose from a uronic acid or a uronic acid from an aldaric acid.

The aldoses obtained by carrying out the method according to the invention are of great interest in themselves but would particularly be very important intermediate chemicals in synthesis if it were to come about that they could be produced in a great quantity and at a low cost. In fact, a simple complementary stage of hydrogenation of these aldoses makes it possible easily to obtain the corresponding alditols which are all polyols able to be used in multiple applications, and particularly as substitutes for saccharine which are low-calorie and do not cause caries.

The dialdoses obtained by putting into practice the method according to the invention, as polyhydroxylated compounds with two aldehyde functions, are equally potentially important intermediate chemicals in synthesis, in particular for the manufacture of aldaric acid by simple oxidation of aldehyde functions.

Finally, the uronic acids obtained by carrying out the method according to the invention, as polyhydroxycarboxylic acids, have sequestering properties capable of being exploited in the field of cements, mortars or cements in which such acids have been suggested as agents to retard setting, or even in the field of detergency where these acids have been proposed for cleaning articles made of glass or metal, or as additives for detergents.

It is in studying the method explained by RUFF, almost a century ago (Ber. 32, 3674, (1889); 33, 1799 (1900)), that the Applicant has perfected a new method of manufacturing an aldose or an aldose derivative, by a chemical process, starting with an acid derivative of monosaccharide or from its salts.

RUFF's method makes it possible to pass, in a general manner, from an aldonic acid containing n carbons to an aldose containing (n−1) carbons thanks to the combined action of ferric ions and of oxygenated water. However the yields of aldose are very modest. Thus the conversion of gluconic acid into D-arabinose is realised according to this method.

Some improvements have, subsequently, been provided by R. C. Hockett and C. S. Hudson (J. Amer. Chem. Soc. 56, 1632–1633, (1934) and ibid. 72, 4546, (1950)) and by the document U.S. Pat. No. 3,755,294. Yields of 60% of arabinose starting with gluconic acid are described there. Progress has been made by V. Bilik (CZ-232647, (1983)), using cupric ions (Cu (II)) as catalysts. Yields in the order of 70% have been reached after laborious purification.

Identical results have been obtained recently with a mixture of ferric and ferrous ions as catalysts (CZ-279002, (1994)).

Finally in particular conditions, document EP-A 0.716.067 reports yields of 78% in certain aldoses.

During an extensive investigation of RUFF's reaction, the Applicant discovered that the salts of cobalt as well as those of ruthenium and of nickel catalysed the reaction of an aldonic acid with n+2 carbon atoms with oxygenated water to give, in a surprising manner, a monosaccharide with n carbon atoms and not, as might have been expected, a monosaccharide with n+1 carbon atoms. There is therefore the loss of two carbon atoms in relation to the initial aldonic acid.

In pursuing its investigations, the Applicant discovered that the salts of cobalt, of ruthenium or of nickel equally catalyzed the reaction of uronic acids or aldaric acids with oxygenated water in order to give, in an unexpected manner, a dialdose or a uronic acid, respectively.

In the same way as previously, the method according to the invention makes it possible to obtain a dialdose with n carbon atoms starting from a uronic acid with n+2 carbon atoms, or a uronic acid with n carbon atoms starting from an aldaric acid with n+2 carbon atoms. In all these cases, there is the loss of two carbon atoms in relation to the initial uronic acid or aldaric acid.

Thus, according to the invention, the method of manufacturing an aldose or an aldose derivative, with n carbon atoms, is characterised by the fact that an aqueous solution of a salt of an acid derivative of monosaccharide with n+2 carbon atoms containing at least one α-hydroxy acid unit, except for gluconic acid, is brought into contact with hydrogen peroxide in the presence of at least one salt of a metal chosen from the group consisting of cobalt, of nickel and of ruthenium.

The method of the invention thus uses a salt of an acid derivative of monosaccharide.

In the present invention what is meant by acid derivative of monosaccharide is a mono- or dicarboxylic acid derived from an aldose. This definition encompasses in particular:
- the aldonic acids which are monocarboxylic acids derived from the aldoses by replacing the aldehyde group with a carboxy group such as maltobionic, lactobionic, glucoheptonic, mannonic, idonic, galactonic, lyxonic, xylonic, arabinonic and ribonic acids, with the exception of gluconic acid;
- the uronic acids containing an α-hydroxy acid unit, which are monocarboxylic acids derived from aldoses by replacing the $CH_2OH$ group with a carboxy group, in which the aldehyde group has been protected, such as glucuronic, iduronic, xyluronic and arabinuronic acids;
- the aldaric acids which are dicarboxylic acids derived from aldoses by replacing the two terminal groups (CHO and $CH_2OH$) with carboxy groups, such as glucaric acid and xylaric acid.

In the present invention, what is meant by the salt of an acid derivative of monosaccharide, is the acid derivative in its free form, in lactonised form, or in the form of a mixture of these two forms, in the form of salts or in the form of esters. Thus, for example, calcium or sodium salts, or the γ- and δ-lactones of these acid derivatives of monosaccharides are perfectly suitable.

The aldonic acids are obtained in known fashion by oxidation of the corresponding monosaccharide. This oxidation stage can be carried out either by a chemical process or by a microbiological process.

The chemical process preferred within the framework of the invention consists in oxidising the monosaccharide with the aid of air or of oxygen in an alcali medium and with the aid of palladium catalysts.

A particularly preferred method is the one which has been described in the document U.S. Pat. No. 4,845,208, of which the Applicant is an assignee, and which consists in using as an oxidation catalyst, palladium fixed on activated charcoal and doped with bismuth.

It can be equally envisaged that the monosaccharide is oxidised by an electrolytic process or with the aid of hypobromite. In addition, it is possible to oxidise the monosaccharide by a microbiological process with the aid of Gluconobacter or Aspergillus.

The uronic acids can be obtained, in known fashion, either by a microbiological process with the aid of *Penicillium brevicompactum, Ustiulina vulgaris* or *Acetobacter melanogenum*, or by a chemical process by hydrolysis of the polyglycuronic acids.

The aldaric acids can be obtained, in known fashion, by oxidation in air, in the presence of platinum, of the corresponding monosaccharides.

By preference, the method of the invention is carried out, in water, with a content of dry matter in the salt of the acid derivative of monosaccharide consisting of between 1 and 60%, preferably between 5 and 50% and more particularly between 10 and 30%.

The constraints on the lower amount of dry matter are imposed for obvious reasons of saving on evaporation of the water and of reducing the size of the reactors.

The constraints on the higher amount of dry matter are essentially imposed by problems of solubility or of viscosity of the reaction medium.

In the present description, all the percentages are expressed in relation to the acid derivative of monosaccharide (example: 50 mol % signifies 50 moles of X for 100 moles of acid derivative of monosaccharide, and 50% signifies 50 g of X for 100 g of initial acid derivative of monosaccharide).

In the method according to the invention, the catalyst is constituted by cobalt ions, ruthenium ions or nickel ions which can be provided in the form of any kind of salt of cobalt, of ruthenium or of nickel. Advantageously, the salts of cobalt are preferred: acetate, acetyl acetonate, halides, nitrate, sulphate, . . . of cobalt are perfectly suitable for example.

A quantity of catalyst of between 0.001 and 50%, preferably between 0.002 and 20% and more particularly between 0.005 and 5% in relation to the salt of the acid derivative of monosaccharide used gives good results in the method according to the invention, in respect of the yield and of the purity of the aldose or of the aldose derivative.

To the salt mixture of acid derivative of monosaccharide, of catalyst and of water thus realised, there is slowly added, with stirring, hydrogen peroxide, preferably in the form of oxygenated water of a strength of 30%, at a ratio of 1 to 500 mol % preferably of 50 to 400 mol % and more particularly of 100 to 300 mol % in relation to the salt of the gluconic acid used.

It is possible to use hydrogen peroxide in the form of oxygenated water in a strength greater than 30%, particularly for example up to 70%.

The oxygenated water is added at an introduction speed such that the temperature of the reaction medium does not rise, preferably, beyond 50° C. and more particularly beyond 40° C. Thus the introduction speed of the oxygenated water is generally situated between 30 minutes and two hours.

By preference, the method of the invention is carried out at a temperature of between 0 and 100° C. and preferably between 10 and 50° C.

Lower temperatures lead to reaction times which are too long, and higher temperatures, in addition to the fact that they would necessitate the use of reactors resistant to pressure, would lead to a degradation of the reaction products.

The temperatures of 20–40° C. are thus particularly preferred in the method of the invention.

By preference too, the method of the invention is carried out at a pH of between 2 and 12, preferably between 5 and 8 and more particularly between 6 and 7.

The invention will be better understood with the aid of the following examples which are intended solely to illustrate the invention better without in any way wishing to limit it to the forms of embodiment expressly described and just to the acid derivatives of monosaccharide used.

In the following examples, all the results are expressed in molar percentage.

EXAMPLE 1

Synthesis of D-threose

Calcium galactonate pentahydrate (130.1 g/0.25 mole), cobalt chloride hexahydrate (0.23 g/0.98 mmole) and water (1000 ml) are introduced into a double envelope reactor. The mixture is raised to a temperature of 35° C. and to a pH of 6.5 by the addition of soda 2N. The water, oxygenated to 35% (129 ml/1.5 moles), is introduced over 75 minutes, maintaining the temperature between 35 and 40° C. and the pH at 6.5 with the aid of soda 2N. When the addition has been completed, the solution is agitated for a further hour. The pH is brought to 2.5 by the addition of concentrated sulphuric acid (14 ml) in order to precipitate salts of calcium. After filtration, the pink solution has the following composition:

D-threose: 85% galactonic acid: 7%.

EXAMPLE 2

Synthesis of D-arabinose

Sodium glucoheptonate dihydrate (71.3 g/0.25 mole), cobalt chloride hexahydrate (0.12 g/0.50 mmole) and water (500 ml) are introduced into a double envelope reactor. The mixture is brought to a temperature of 30° C. and to a pH of 6.5 by the addition of soda 2N. The water, oxygenated to 30% (77 ml/0.75 mole), is introduced over 75 minutes, maintaining the temperature between 30 and 35° C. and the pH at 6.5 with the aid of soda 2N. When the addition is finished, the solution is agitated for a further hour. The pH is brought to 2.5 by the addition of concentrated sulphuric acid (8 ml). The pink solution has the following composition:

D-arabinose: 71.9%, glucoheptonic acid: 11.7%.

EXAMPLE 3

Synthesis of D-glyceraldehyde

Sodium arabinonate (47.9 g/0.255 mole), cobalt chloride hexahydrate (1.03 g/4.33 mmoles) and water (500 ml) are introduced into a double envelope reactor. The mixture is brought to a temperature of 25° C. and to a pH of 6.5 by the addition of soda 2N. The water, oxygenated to 30% (55 ml/0.54 mole), is introduced over 75 minutes, maintaining the temperature between 25 and 30° C. and the pH at 6.5 with the aid of soda 2N. When the addition has been finished, the solution is agitated for a further hour. The pH is brought to 2.5 by the addition of concentrated sulphuric acid (14 ml). The pink solution has the following composition:

D-glyceraldehyde: 30%,
arabinonic acid: 43%,
erythronic acid: 9%.

EXAMPLE 4

Synthesis of glucosyl-1,2-erythrose

Calcium maltobionate (75.2 g/0.1 mole), cobalt chloride hexahydrate (0.38 g/1.6 mmoles) and water (300 ml) are introduced into a double envelope reactor. The mixture is brought to a temperature of 30° C. and to a pH of 6.5 by the addition of soda 2N. The water, oxygenated to 35%, (52 ml/0.6 mole) is introduced over 75 minutes, maintaining the temperature between 30 and 35° C. and the pH at 6.5 with the aid of soda 2N. When the addition is finished, the solution is agitated for a further hour. The pH is brought to 2.5 by the addition of concentrated sulphuric acid (14 ml) in order to precipitate salts of calcium. After filtration, the pink solution contains glucosyl-1, 2-erythrose with a molar yield of 85%.

EXAMPLE 5

Synthesis of tetruronic Acids

Potassium glucarate monosalt (63.2 g/0.255 mole), cobalt chloride hexahydrate (1.3 g/5.46 mmoles) and water (500 ml) are introduced into a double envelope reactor. The mixture is brought to a temperature of 25° C. and to a pH of 6.5 by the addition of soda 2N. The water, oxygenated to 30%, (55 ml/0.54 mole), is introduced over 75 minutes, maintaining the temperature between 25 and 30° C. and the pH at 6.5 with the aid of soda 2N. When the addition is completed, the solution is agitated for a further hour. The pH is brought to 2.5 by the addition of concentrated sulphuric acid (14 ml). The pink solution has the following composition:

tetruronic acids (threuronic and erythruronic): 44%
glucaric acid: 23%

I claim:

1. A method of manufacturing an aldose or an aldose derivative, with n carbon atoms, comprising contacting an aqueous solution of a salt of an acid derivative of a monosaccharide with n+2 carbon atoms containing at least one α-hydroxy carboxylic acid moiety with the exception of gluconic acid, with hydrogen peroxide in the presence of at least one salt of a metal chosen from the group consisting of cobalt, nickel and ruthenium.

2. A method of manufacture according to claim 1, wherein the aqueous solution has a salt dry matter of the acid derivative of monosaccharide with n+2 carbon atoms containing at least one α-hydroxy carboxylic acid moiety of between 1 and 60 wt. %.

3. A method of manufacture according to claim 1, wherein the metal salt is present in a quantity of between 0.001 and 50% expressed in relation to the salt of the acid derivative of monosaccharide with n+2 carbon atoms containing at least one α-hydroxy carboxylic acid moiety.

4. A method of manufacture according to claim 1, wherein hydrogen peroxide is used in a quantity of between 1 and 500 mol % expressed in relation to the salt of the acid derivative of monosaccharide with n+2 carbon atoms containing at least one α-hydroxy carboxylic acid moiety.

5. A method of manufacture according to claim 1, wherein the process is carried out at a temperature of between 0 and 100° C.

6. A method of manufacture according to claim 5, wherein the process is carried out at a temperature of between 10 and 50° C.

7. A method of manufacture according to claim 1, wherein the process is carried out at a pH of between 2 and 12.

8. A method of manufacture according to claim 7, wherein the process is carried out at a pH of between 5 and 8.

9. A method of manufacturing an aldose according to claim 1, wherein the salt of an acid derivative of monosaccharide with n+2 carbon atoms containing at least one α-hydroxy carboxylic acid moiety is a salt of an aldonic acid.

10. A method of manufacturing a dialdose according to claim 1, wherein the salt of an acid derivative of monosaccharide with n+2 carbon atoms containing at least one α-hydroxy carboxylic acid moiety is a salt of a uronic acid.

11. A method of manufacturing a uronic acid according to claim 1, wherein the salt of an acid derivative of monosaccharide with n+2 carbon atoms containing at least one α-hydroxy carboxylic acid moiety is a salt of an aldaric acid.

12. A method of manufacture according to claim 2, wherein the metal salt is present in a quantity of between 0.001 and 50% expressed in relation to the salt of the acid derivative of monosaccharide with n+2 carbon atoms containing at least one α-hydroxy carboxylic acid moiety.

13. A method of manufacture according to claim 2, wherein hydrogen peroxide is used in a quantity of between 1 and 500 mol % expressed in relation to the salt of the acid derivative of monosaccharide with n+2 carbon atoms containing at least one α-hydroxy carboxylic acid moiety.

14. A method of manufacture according to claim 3, wherein hydrogen peroxide is used in a quantity of between 1 and 500 mol % expressed in relation to the salt of the acid derivative of monosaccharide with n+2 carbon atoms containing at least one α-hydroxy carboxylic acid moiety.

15. The process according to claim 4, wherein the hydrogen peroxide is in the form of oxygenated water with a strength of 30%.

16. The process according to claim 13, wherein the hydrogen peroxide is in the form of oxygenated water with a strength of 30%.

17. The process according to claim 14, wherein the hydrogen peroxide is in the form of oxygenated water with a strength of 30%.

* * * * *